United States Patent [19]

Stetter et al.

[11] 4,035,395

[45] July 12, 1977

[54] PROCESS FOR THE PREPARATION OF KETONES

[75] Inventors: Hermann Stetter; Heinrich Kuhlmann, both of Aachen-Laurensberg, Germany

[73] Assignee: Bayer Aktiengesellschaft, Leverkusen, Germany

[21] Appl. No.: 598,605

[22] Filed: July 24, 1975

[30] Foreign Application Priority Data

Aug. 2, 1974 Germany .......................... 2437219

[51] Int. Cl.² ................ C07D 307/46; C07C 49/00
[52] U.S. Cl. ..................... 260/347.5; 260/347.8; 260/465 R; 260/465.1; 260/476 R; 260/483; 260/586 C; 260/590 R; 260/592; 260/593 R
[58] Field of Search ........ 260/347.8, 586 C, 593 R, 260/590 R, 483, 465.1

[56] References Cited

U.S. PATENT DOCUMENTS

| 2,577,133 | 12/1951 | Ladd | 260/483 |
| 2,594,489 | 4/1952 | Patrick | 260/465.1 |
| 2,621,212 | 12/1952 | Ladd | 260/593 R |
| 3,865,881 | 2/1975 | McMullen | 260/593 R |

OTHER PUBLICATIONS

Stetter et al. I, Angew. Chem. Internat. Edit., vol. 12, (1973) p. 81.
Stetter et al. II, Tetrahedron Letters No. 17, pp. 1461–1462 (1973).
Stetter et al. III, Chem. Ber. vol. 107, pp. 210–214, (1974).

Primary Examiner—Henry R. Jiles
Assistant Examiner—Bernard Dentz
Attorney, Agent, or Firm—Burgess, Dinklage & Sprung

[57] ABSTRACT

The invention concerns a new process for the preparation of ketones; according to this process ketones are prepared from aldehydes and unsaturated compounds in the presence of bases using quaternary ammonium salts as catalysts.

18 Claims, No Drawings

PROCESS FOR THE PREPARATION OF KETONES

The invention relates to a process for the preparation of ketones from aldehydes and unsaturated compounds.

According to the present invention ketones are obtained by reacting unsaturated compounds of the formula

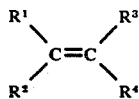

wherein
$R^1$, $R^2$ and $R^3$ are identical or different and represent hydrogen or an optionally substituted aliphatic, cycloaliphatic, araliphatic, aromatic or heterocyclic radical or a carboxylic acid ester group, and
$R^4$ represents the nitrile radical or the groups —CO—$R^5$ and —CO—O—$R^5$
wherein
$R^5$ denotes an optionally substituted aliphatic, araliphatic, aromatic or heterocyclic radical and
wherein
it is also possible for $R^1$ and $R^2$ or $R^3$, $R^2$ and $R^4$, and $R^3$ and $R^4$ to be bonded to one another directly, with formation of a carbocyclic or heterocyclic ring, with aldehydes in the presence of quaternary ammonium salts as catalysts, with addition of bases, and if appropriate, in the presence of a solvent.

The process according to the invention can be illustrated by the following equation for the reaction of methyl vinyl ketone and n-butyraldehyde:

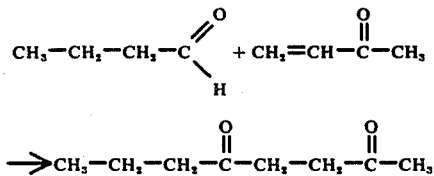

Examples of suitable optionally substituted aliphatic radicals for the groups $R^1$, $R^2$, $R^3$ and $R^5$ which may be mentioned are straight-chain or branched aliphatic radicals with up to 12, preferably with up to 6, carbon atoms. For example, the methyl, ethyl, isopropyl, propyl, butyl, tert.butyl, pentyl, hexyl, octyl, nonyl, decyl and dodecyl radical, preferably the methyl, ethyl and isopropyl radical, are suitable.

Examples of suitable optionally substituted cycloaliphatic radicals for the groups $R^1$, $R^2$, $R^3$ and $R^5$ are those with 3 to 18, preferably 4 to 12, and especially preferentially 5 and 6, carbon atoms, such as, for example, the cyclopropyl, cyclobutyl, cyclopentyl, cyclohexyl, cycloheptyl, cyclooctyl, cyclododecyl, cycloheptadecyl and cyclooctadecyl radical, preferably the cyclopentyl and cyclohexyl radical.

Examples of suitable optionally substituted araliphatic radicals for the groups $R^1$, $R^2$, $R^3$ and $R^5$ are those with 6 to 18 carbon atoms of which the aliphatic part contains 1 to 6 carbon atoms and of which the aromatic part represents a radical of the benzene series. The following araliphatic radicals may be mentioned by way of examples: the benzyl, β-phenylethyl, γ-phenylpropyl, β-phenyl-n-hexyl, β-[naphthyl-(1)]-ethyl, ω-phenylbutyl, ω-phenylpentyl and ω-phenylhexyl radical, preferably the benzyl and γ-phenylpropyl radical.

Examples of suitable optionally substituted aromatic radicals from the groups $R^1$, $R^2$, $R^3$ and $R^5$ are radicals of the benzene series, such as the phenyl radical, the naphthyl radical, the phenanthracyl radical, the tetracyl radical, the anthracyl radical and the biphenyl radical, preferably the phenyl and the naphthyl radical.

Examples of suitable optionally substituted heterocyclic radicals for the groups $R^1$, $R^2$, $R^3$ and $R^5$ are 5-membered or 6-membered rings which in addition to hdyrocarbon members contain one or more heteroatoms, such as, for example, nitrogen, oxygen and/or sulphur. The heterocyclic radicals can be aromatic or wholly or partially hydrogenated and can in addition be fused to one or more radicals from the benzene series. Examples of heterocyclic radicals which may be mentioned are the pyrrole, furane, thiophene, indole, coumarane, thionaphthene, pyridine, pyrone, oxazole, imidazole, benzoxazole, benzimidazole, benzthiazole, quinoline, isoquinoline, piperidine, pyrrolidine and tetrahydrofurane radical, preferably the pyridine, furane, thiophene and quinoline radical.

If $R^1$ and $R^2$ or $R^3$, $R^2$ and $R^4$, and $R^3$ and $R^4$, are linked directly to form a ring, the ring can be either carbocyclic or heterocyclic, the heterocyclic ring systems having the definition given above for $R^1$, $R^2$, $R^3$ and $R^5$. Possible carbocyclic radicals are rings containing saturated and unsaturated hydrocarbon members, preferably 5-membered or 6-membered rings.

Possible substituents of the aliphatic, cycloaliphatic, araliphatic and aromatic radicals are substituents which do not change under the reaction conditions.

Examples of suitable substituents are the halogens, such as fluorine, chlorine, bromine and iodine, the cyano group, the nitro group, the amino group, which can be monosubstituted or disubstituted by alkyl or aryl radicals, such as the methylamino, dimethylamino, phenylamino, diethylamino, N-piperidino and N-morpholino group, straight-chain or branched alkyl radicals containing 1 to 6 carbon atoms, such as the methyl, ethyl, propyl, isopropyl, pentyl, hexyl and iso-hexyl radical, aryl radicals from the benzene series, such as the phenyl and the naphthyl radical, the hydroxyl group, $C_1$ to $C_6$ alkoxy groups, such as the methoxy and ethoxy group, $C_1$ to $C_6$ alkylmercapto groups, such as the methylmercapto and ethylmercapto group, $C_1$ to $C_6$ carboxylic acid ester and thiocarboxylic acid ester groups, such as the methylcarboxylate, ethylcarboxylate, methylthiocarboxylate and ethylthiocarboxylate radical, and the $C_1$ to $C_{10}$ alkylcarbonyl and arylcarbonyl groups, such as the benzoyl, acetyl and isobutyryl groups.

The unsaturated compounds of the formula I which can be used for the process according to the invention, are in general known compounds. As examples there may be mentioned methyl vinyl ketone, phenyl vinyl ketone, β-naphthyl vinyl ketone, benzalacetone, dibenzalacetone, benzalpinacoline, 1-benzalcyclopentanone-(2), benzalacetophenone, 4'-nitrochalcone, 4'-dimethylaminochalcone, 2'-hydroxy-4'-methylchalcone, β-pyridyl-β-styryl ketone, 3-nitrochalcone, p-anisalcyclopentanone, furfural-acetone, 1-(α-pyridyl)-3-phenyl-propene-(3), mesityl oxide, cyclopentenone, cyclohexenone, acrylic acid esters, crotonic acid esters, maleic acid esters, cinnamic acid esters, α-pyridylacrylic acid esters, furfurylidenacetic acid esters, cyclohexene(1)-carboxylic acid esters, p-nitrocinnamic acid esters, acrylonitrile, methacrylonitrile, crotonic acid nitrile, cinnamic acid nitrile and cyclopentene(1)-carboxylic acid nitrile.

It is also possible to use, in place of the unsaturated compounds, mentioned in formula I, compounds of the formula

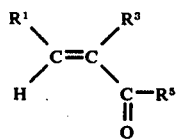   II wherein $R^1$, $R^3$ and $R^5$ have the abovementioned meaning, compounds which decompose under the reaction conditions to give the unsaturated compounds of the formula II. As examples there may be mentioned (a) Mannich bases of the formula

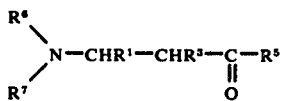   III wherein $R^1$, $R^3$ and $R^5$ have the abovementioned meaning and $R^6$ and $R^7$ are identical or different and represent an aliphatic radical or can also be linked directly to one another, and (b) β-halogenocarbonyl compounds of the formula

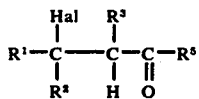   IV wherein

Hal represents chlorine, bromine or iodine and $R^1$, $R^3$ and $R^5$ have the abovementioned meaning.

Possible aliphatic radicals $R^6$ and $R^7$ are, for example, those with up to 6, preferably with up to 3, carbon atoms. The following aliphatic and heterocyclic radicals may be mentioned as examples: the methyl, ethyl, propyl, butyl, hexyl, pyrrole, pyridine and piperidine radical.

The following may be mentioned as examples of Mannich bases: N,N-dimethyl-β-benzoyl-ethylamine, N-(3-oxobutyl)-piperidine and N,N-diethyl-β-pivaloyl-ethylamine.

The following may be mentioned as examples of β-halogenocarbonyl compounds: β-chloropropiophenone, β-chloropropionic acid ethyl ester, 1,3-dichloro-2-benzoylpropane and α,β-dichloropropionic acid ethyl ester.

The aldehyde used in the process according to the invention may be any aliphatic, aromatic or heterocyclic compound which is substituted by an aldehyde group. The aldehydes in general correspond to the formula

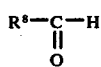   V wherein $R^8$ represents hydrogen or an optionally substituted aliphatic, cycloaliphatic, araliphatic, aromatic or heterocyclic radical.

If the radical $R^8$ is an aliphatic radical, it can be, for example, a straight-chain or branched radical with up to 20 carbon atoms. Examples which may be mentioned are the methyl, ethyl, n-propyl, isopropyl, n-butyl, tert.-butyl, isoamyl, hexyl, heptyl, octyl, nonyl, decyl, dodecyl, myristyl, palmyl, cetyl and stearyl radical.

If the radical $R^8$ is a cycloaliphatic radical, examples which may be mentioned are cycloaliphatic radicals with 3 to 18 carbon atoms, such as the cyclopropyl, cyclobutyl, cyclopentyl, cyclohexyl, cycloheptyl, cyclooctyl, cyclononyl, cyclodecyl, cyclododecyl, cycloheptadecyl and cyclooctadecyl radical.

Possible araliphatic radicals are, for example, radicals with 7 to 18 carbon atoms, which contain up to 6 carbon atoms in the aliphatic part. The benzyl, ω-phenyl ethyl, ω-phenylpropyl, ω-phenylbutyl, ω-phenylpentyl, ω-phenylhexyl, diphenylethyl, β-[naphthyl-(2)]-methyl and β-[naphthyl (2)]-ethyl radical may be mentioned as examples.

Possible aromatic radicals are, for example, radicals from the benzene series, having 6 to 20 carbon atoms. The phenyl, naphthyl(2), anthranyl(9), tetracyl(2), chrysyl(2), pyrenyl(4) and 3,4-benzpyrenyl(2) radical may be mentioned as examples.

Possible heterocyclic radicals are, for example, 5-membered or 6-membered rings which in addition to carbon members contain one or more hetero-atoms, such as nitrogen, oxygen and/or sulphur. In addition, the heterocyclic radicals can be fused to a benzene ring. Examples of heterocyclic radicals which may be mentioned are the pyrrolyl, furyl, thiophenyl, indolyl, coumaronyl, thionaphthyl, pyrazolyl, imidazolyl, oxazolyl, thiazolyl, pyridyl, quinolyl, thienyl and tetrahydrofuryl radical.

The aliphatic, cycloaliphatic, araliphatic, aromatic and heterocyclic radicals can carry any substituents which are inert under the reaction conditions. Examples of substituents which may be mentioned are the halogens, such as fluorine, chlorine, iodine and bromine, the cyano group, the nitro group, the amino group, which can, for example, be monosubstituted or disubstituted by alkyl or aryl radicals, such as the methylamino, dimethylamino, phenylamino, diethylamino, N-piperidino and N-morpholino group, straight-chain or branched alkyl radicals containing 1 to 6 carbon atoms, such as the methyl, ethyl, propyl, iso-propyl, pentyl, hexyl and iso-hexyl radical, aryl radicals from the benzene series, such as the phenyl and the naphthyl radical, the hydroxyl group, the aldehyde group, $C_1$ to $C_6$ alkoxy groups, such as the methoxy and ethoxy group, $C_1$ to $C_6$ alkylmercapto groups, such as the methylmercapto and ethylmercapto group, $C_1$ to $C_6$ carboxylic acid ester and thiocarboxylic acid ester groups, such as the methylcarboxylate, ethylcarboxylate, methylthiocarboxylate and ethylthiocarboxylate radical, and $C_1$ to $C_{10}$ alkylcarbonyl and arylcarbonyl groups, such as the isobutyryl and benzoyl group.

Preferred aldehydes of the formula (V) which can be employed in accordance with the process of the invention are compounds of the formula

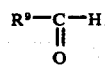   VI wherein $R^9$ represents a $C_1$ to $C_{12}$ aliphatic radical or a $C_5$ to $C_{12}$ cycloaliphatic radical or a $C_7$ to $C_{12}$ araliphatic radical which contains up to 6 carbon atoms in the aliphatic part, a $C_6$ to $C_{10}$ aromatic radical or a 5-membered ring which in addition to carbon atoms contains an oxygen atom and/or a sulphur atom.

Particularly preferred aldehydes are those of the formula

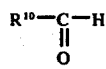     VII wherein $R^{10}$ represents the methyl, ethyl, propyl or isopropyl radical, the cyclohexyl radical, the benzyl or β-[naphthyl-(2)]-methyl radical, the phenyl or naphthyl radical or the furyl radical.

The aldehydes which can be used for the process according to the invention are, in general, known compounds. Examples which may be mentioned are: formaldehyde, acetaldehyde, propionaldehyde, isobutyraldehyde, n-butyraldehyde, n-valeraldehyde, pivalinaldehyde, iso-valeraldehyde, capronaldehyde, oenanthaldehyde, 2-ethylhexanal, caprylaldehyde, pelargonaldehyde, caprinaldehyde, laurinaldehyde, myristinaldehyde, levulinaldehyde, 3-phenylpropanal, succindialdehyde, glutarodialdehyde, adipodialdehyde, glucose, benzaldehyde, 4-chlorobenzaldehyde, 2-chlorobenzaldehyde, 4-bromobenzaldehyde, 4-iodobenzaldehyde, 4-fluorobenzaldehyde, 2-, 3- and 4-nitrobenzaldehyde, 2,4-dinitro-benzaldehyde, salicylaldehyde, 2-, 3- and 4-methoxybenzaldehyde, 4-carbethoxybenzaldehyde, 2-, 3- and 4-methylbenzaldehyde, 2-, 3- and 4-ethylbenzaldehyde, α- and β- naphthaldehyde, furfuraldehyde, pyrrol-2-aldehyde, thiophen-3-aldehyde, pyrazol-3-aldehyde, imidazol-4-aldehyde, benzimidazol-3-aldehyde, oxazol-4-aldehyde, pyridin-2-aldehyde, pyridin-3-aldehyde, pyridin-4-aldehyde, 2-methylpyridin-3-aldehyde, quinolin-5-aldehyde, quinolin-2-aldehyde, isoquinolin-1-aldehyde and uracil-6-aldehyde.

It is also possible to use, within the scope of the aldehydes mentioned in formula V, compounds which decompose to the aldehydes under the reaction conditions, such as, for example, the acyloins or the benzoins of the formula

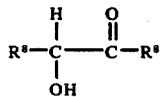     VIII wherein $R^8$ has the abovementioned meaning.

Examples of possible acyloins or benzoins are benzoin, acetoin, n-butyroin and captronin.

The process according to the invention is carried out in the presence of a quaternary ammonium salt as the catalyst, and with addition of a base.

Examples of suitable quaternary ammonium salts are compounds of the formula

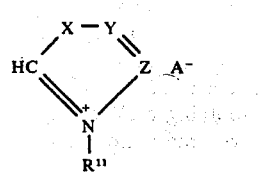     IX wherein

X represents oxygen, sulphur, selenium or the —$NR^{12}$— group, and

Y and Z are identical or different and represent optionally substituted carbon atoms and/or nitrogen atoms, $R^{11}$ and $R^{12}$ are identical or different and have the same range of meaning as $R^8$ and A represents an acid radical.

If Y and Z are carbon atoms, these are substituted, for example by hydrogen, the halogens, such as fluorine, chlorine, bromine and iodine, the nitro group, the cyano group, the carbonyl group, the carboxyl group, the carboxylic acid ester group, the carboxylic acid amide group or other radicals which have the same meaning as $R^8$. However, it is also possible for Y and Z to be linked to one another by hydrocarbon members and thus to form a radical of the benzene series.

Examples of possible anions of the quaternary ammonium salts are the halide ions, such as fluoride, chloride, bromide or iodide, the sulphate ion, the phosphate ion or organic anions, such as phenylsulphonate or oxalate. Preferably, the chlorides, bromides or iodides are employed.

Preferred catalysts for the process according to the invention are thiazolium salts, imidazolium salts, benzimidazolium salts, selenazolium salts, triazolium salts, oxazolium salts and thiadiazolium salts.

A suitable method for the preparation of the catalysts is described in J. Am Chem. Soc. 66, 652 (1944).

For example, the following quaternary ammonium salts can be employed for the process according to the invention: 5-(2'-hydroxyethyl)-4-methyl-3-benzyl-thiazolium chloride, 5-(2'-hydroxyethyl)-4-methyl-3-ethyl-thiazolium bromide, 1,3-dimethylimidazolium iodide, 1,3-dimethylbenzimidazolium iodide, 3-benzyl-1,3,4-thiadiazolium iodide, benzthiazoline bromide.

Further possible catalysts for the process according to the invention are the polymers and polycondensates in which the ammonium salts defined above are part of the polymeric molecule. For example, poly-3,4-diethyl-5-vinyl-thiazolium iodide can be employed as the catalyst.

Weak inorganic and/or organic bases can be employed as bases for the process according to the invention. Possible inorganic bases are, for example, the basic salts of the alkali metals and alkaline earth metals, such as the carbonates, phosphates, borates or acetates.

Examples of suitable organic bases are the amines of the formula

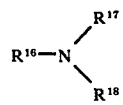     X wherein $R^{16}$, $R^{17}$ and $R^{18}$ are identical or different and have the same range of meaning as $R^8$.

For example, the following bases can be employed for the process according to the invention: sodium carbonate, potassium carbonate, disodium hydrogen phosphate, triethylamine, triethanolamine and N-methyl-pyrrolidine.

To carry out the process according to the invention, the unsaturated compound of the formula I and the aldehyde are in general employed in equimolar amounts. However, the unsaturated compound or the aldehyde can also be employed in excess.

If, instead of the aldehyde, the corresponding acyloin or benzoin is used, only half the molar amount need be employed.

The amount of catalyst employed is not critical. In general, the process according to the invention is carried out in the presence of 1 to 50 mol %, preferably of 5 to 20 mol %, and especially preferentially of 5 to 12 mol %, relative to the aldehyde employed. However, even amounts of less than 1 mol % can suffice for carrying out the process.

The amount of the base employed is also not critical but in general at least an amount equimolar to the catalyst is employed. Preferably, a 3-molar to 5-molar amount, relative to the catalyst employed, is used.

The process according to the invention can be carried out with or without solvents. For carrying out the process in solvents, polar solvents, such as methanol, ethanol, isopropanol, dioxane, acetonitrile, dimethylformamide, dimethylsulphoxide, hexamethylphosphoric acid amide and pyridine, preferably ethanol and dimethylformamide, can be used.

The solvents can be employed individually or as mixtures.

If the process is carried out without a special solvent, an excess of a starting compound can be used as the reaction medium.

While it is not essential to carry out the process according to the invention under anhydrous conditions, it is expedient to carry it out in anhydrous solvents.

The process according to the invention can be carried out at a temperature of $-10°$ to $100°$ C, preferably of $35°$ to $90°$ C, and particularly preferentially of $50°$ to $80°$ C.

Advantageously, oxygen is excluded when carrying out the process according to the invention, for example by blanketing the reaction mixture with nitrogen.

In general, the reaction is carried out as follows: the aldehyde, the unsaturated compound and the catalyst are dissolved in a solvent and the particular base is added. The mixture is stirred briefly and is then brought to the reaction temperature.

However, it is also possible to add the dissolved unsaturated compound dropwise, while stirring, to the mixture of the remaining components.

A converse procedure is also possible, that is to say first to take the unsaturated compound and to add the aldehyde dropwise.

After completion of the reaction, the products are isolated in a manner which is in itself known.

In general it is expedient to remove the solvent in a slight vacuum and to reuse it after suitable working up. The residue is taken up in a suitable water-immiscible solvent, such as methylene chloride, chloroform and/or benzene and the solution is then washed with water and sodium bisulphite solution. The reaction product is isolated from the organic phase in a conventional manner, for example by distilling off the solvent. The reaction product thus obtained can furthermore be purified in a conventional manner, for example by recrystallization, distillation and/or chromatography.

Using the process according to the invention, ketones of the formula

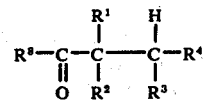

wherein $R^1$, $R^2$, $R^3$, $R^4$ and $R^8$ have the abovementioned meanings are in general obtained.

When using formaldehyde, ketones of the formula

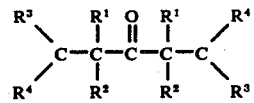

wherein $R^1$, $R^2$, $R^3$ and $R^4$ have the abovementioned meanings are obtained within the framework of the process according to the invention.

For example, the following ketones may be obtained: decane-2,5-dione, undecane-2,5-dione, octane-2,5-dione, 6-methyl-heptane-2,5-dione, acetonyl-acetone, 1,3-diphenyl-heptane-1,4-dione, nonane-2,5,8-trione, α-furoylpropionic acid ethyl ester, α-furoylpropionitrile, 1-phenyl-pentane-(1,4)-dione, 1,2,4-triphenyl-butane-1,4-dione, 2-phenyl-1,4-(2'-furyl)-butane-1,4-dione, 1,3-diphenyl-1,4-dioxoheptane, 1-(2'-furyl)-2,4-diphenyl-1,4-dioxobutane and levulinic acid nitrile.

The following Examples illustrate the invention.

the following catalysts are employed in Examples 1 to 45:

Catalyst 1 (Cat. 1): 5-(2'-hydroxyethyl)-4-methyl-3-benzylthiazolium chloride.
Catalyst 2 (Cat. 2): 5-(2'-hydroxyethyl)-4-methyl-3-ethylthiazolium bromide.
Catalyst 3 (Cat. 3): poly-(5-vinyl)-3,4-dimethylthiazolium iodide (75% quaternized).
Catalyst 4 (Cat. 4): 1,3-dimethylimidazolium iodide.
Catalyst 5 (Cat. 5): 3-benzyl-1,3,4-thiadiazolium chloride.
Catalyst 6 (Cat. 6): thiaminium dichloride.

EXAMPLE 1

12.3 g (0.0455 mol) of Cat. 1, 450 ml of ethanol, 45.7 g (0.455 mol) of capronaldehyde and 32 g (0.455 mol) of methyl vinyl ketone are introduced successively into a 1 l three-necked flask equipped with a stirrer, reflux condenser (with calcium chloride tube) and filling orifice.

After the addition, a dropping funnel fitted with a pressure equilibrator and with an attached gas inlet tube is fitted to the inlet orifice. Dry pure nitrogen is now passed through the apparatus for 15 minutes and thereafter 5.5g(0.0545 mol) of triethylamine, dissolved in 50 ml of ethanol, are added, in a thin stream, to the stirred mixture. The occurrence of a pale yellow coloration, which persists to the end of the reaction, is observed. The mixture is now brought to the reflux temperature while continuing the stirring. At this temperature the reaction mixture is transferred, after 15 hours, into a round flask and the solvent is removed in a slight vacuum. 50 ml of tetrahydrofurane are added to the residue, the mixture is cooled to 0° – 5° C and the solid is filtered off by applying a slight vacuum and is then washed with a very small amount tetrahydrofurane.

After removing the small amount of solvent, the filtrate is distilled in an oil pump vacuum. Decane-2,5-dione is obtained.

Boiling point$_{0.8}$ = 80 – 85° C.
Yield : 51 g ≙ 66% of theory.
Melting point = 18° C (temperature of the melt).
$C_{10}H_{18}O_2$ (molecular weight: 170.24). Calculated: C, 70.54; H, 10.66. Found: C, 70.31; H, 10.83.

EXAMPLE 2

Analogously to the procedure described in Example 1, 9.8 g (0.0364 mol) of Cat. 1, 41.4 g (0.362 mol) of distilled oenanthaldehyde, 25.3 g (0.362 mol) of stabilized methyl vinyl ketone, 400 ml of methanol and 4.4 g (0.0435 mol) of triethylamine are taken and heated for 15 hours under nitrogen at the reflux temperature.

To work up the mixture, the solvent is removed, the cooled residue is filtered by applying a slight vacuum and the filtrate is distilled in an oil pump vacuum. Undecane-2,5-dione is obtained.

Yield: 34.2 g ≙ 51% of theory.
Boiling point (0.75) = 90 – 95° C.
Melting point 33° – 34° C.
$C_{11}H_{20}O_2$ (molecular weight 184.27). Calculated: C, 71.69; H, 10.94. Found: C, 71.64; H, 10.92.

EXAMPLE 3

Following the description in Example 1 and employing the same method, 36 g (0.5 mol) of distilled n-butyraldehyde, 13.5 g (0.05 mol) of Cat. 1, 500 ml of ethanol, 35 g (0.5 mol) of methyl vinyl ketone and 20.2 g (0.2 mol) of triethylamine are taken and heated for 15 hours under nitrogen.

To work up the mixture, the bulk of the ethanol is distilled off initially under normal pressure and then in a waterpump vacuum. The residue is taken up in 250 ml of chloroform and the solution is washed with dilute sodium bisulphite solution and with water. The chloroform is distilled off and the residue is fractionated in an oil pump vacuum. Octane-2,5-dione is obtained.

Yield 51 g ≙ 72% of theory.
Boiling point$_{0.2}$ = 45° – 48° C.
$C_8H_{14}O_2$ (molecular weight 142.19). Calculated: C, 67.57; H, 9.93. Found: C, 67.86; H, 10.07.

EXAMPLE 4

Following the description in Example 1 and employing the same method, 36 g (0.5 mol) of distilled i-butyraldehyde, 13.5 g (0.05 mol) of Cat. 1, 35 g (0.5 mol) of methyl vinyl ketone, 400 ml of methanol and 6 g (0.06 mol) of triethylamine are combined and heated for 12 hours in a nitrogen atmosphere. The mixture is worked up as in Example 2.

Yield 31.2 g ≙ 44% of theory of 6-methyl-heptane-2,5-dione.
Boiling point$_{0.7}$ = 45° – 47° C.
$C_8H_{14}O_2$ (molecular weight 142.19). Calculated: C, 67.57; H, 9.93. Found: C, 67.61; H, 9.98.

EXAMPLE 5

Following the instruction in Example 1, 1.5 l of ethanol, 33 g (0.75 mol) of acetaldehyde freshly prepared from paraldehyde, 13.5 g (0.05 mol) of Cat. 1, 35 g (0.5 mol) of stabilized methyl vinyl ketone and 20.2 g (0.2 mol) of triethylamine are successively introduced into a 2 l three-necked flask and the mixture is heated for 24 hours, while stirring, in a very slight stream of nitrogen.

For working up, the solvent is distilled off under normal pressure and the liquid which remains is distilled as completely as possible in a waterpump vacuum. The colorless liquid which then remains is fractionated through a 30 cm Vigreux column. A first running of 16 g of boiling point$_{760}$ = 142° – 180° C, which predominantly consists of acetoin, and a main fraction of boiling point$_{760}$ = 188° – 194° C, which consists of acetonylacetone, are taken.

Yield = 28 g ≙ 49% of theory.
Boiling point$_{760}$ = 188° – 194° C.

EXAMPLE 6

Following the description in Example 1, 18 g (0.25 mol) of n-butyraldehyde, 52 g (0.25 mol) of benzylideneacetophenone and 500 ml of dimethylformamide, 250 ml of ethanol and 13.5 g (0.05 mol) of Cat. 1 are — after addition of 10.1 g (0.1 mol) of triethylamine — brought to the reflux temperature for 36 hours. To work up the batch, the solvent mixture is distilled off in a waterpump vacuum, the oily residue, when cold, is taken up in 250 ml of chloroform and the solution is washed successively with water, with dilute sodium bisulphite solution and twice more with water. The organic phase is separated off, the chloroform is distilled off and the residue is distilled in an oil pump vacuum. The fraction of boiling point$_{0.2}$ = 140° – 170° C which is thus obtained is subsequently fractionated through a 30 cm Vigreux column. After a first running of benzylideneacetophenone, 1,3-diphenylheptane-1,4-dione is isolated as the main fraction.

Yield: 49.0 ≙ 70% of theory.
Boiling point$_{0.2}$ = 159° – 164° C.
$C_{19}H_{20}O_2$ (molecular weight 280.35). Calculated: C, 81.39; H, 7.19. Found: C, 81.48; H, 7.06.

EXAMPLE 7

Following the procedure described in Example 1, 15 g (0.5 mol) of paraformaldehyde, 13.5 g (0.05 mol) of Cat. 1, 500 ml of ethanol, 35 g (0.5 mol) of stabilized methyl vinyl ketone and 20.2 g (0.2 mol) of triethylamine are brought together and boiled for 20 hours under reflux while stirring under nitrogen. After about 2 hours, all the paraformaldehyde has dissolved.

On working up, the solvent is first distilled off under normal pressure and the last remnants are then removed in vacuo. The reaction product is transferred into a distillation flask and is then distilled in an oil pump vacuum. The partially solid fraction of boiling point$_{0.5}$ = 90° – 130° C is then fractionated through a 10 cm Vigreux column. The product, nonane-2,5,8-trione, is the fraction of boiling point$_{0.5}$ = 110° – 115° C. The product solidifies in the receiver and is recrystallized from a very large amount of n-hexane.

Yield: 11 g ≙ 26% of theory.
Melting point = 57° – 59° C.
Boiling point$_{0.5}$ = 110° – 115° C.

EXAMPLE 8

Following the procedure described in Example 1, 10 g of Catalyst 1 (0.04 mol) and 48 g (0.5 mol) of furfuraldehyde are dissolved in 300 ml of ethanol and 20.2 g (0.2 mol) of triethylamine are then added after displacing the air by After a delay of a few seconds, the reaction mixture assumes a blood-red coloration and after about 15 minutes, when the temperature rises, furoin precipitates as a solid. After about 45 minutes, the exothermic reaction has ended. The mixture is then heated to 70° C and 50 g (0.5 mol) of acrylic acid ester are added dropwise over the course of 2½ hours. The mixture is stirred for 12 hours under a very slight stream of nitrogen.

For working up, the reaction mixture is first separated, in vacuo, from alcohol and unconverted starting compounds, the residue is taken up in 250 ml of chloroform, the solution is washed in a separating funnel with sodium bisulphite solution and water, the organic phase is separated off, the solvent is distilled off and the residue is then distilled in an oil pump vacuum. α-Furoylpropionic acid ethyl ester is obtained.

Yield: 41 g ≙ 42% of theory.
Boiling point $_{0.5}$ = 115°–120° C.
Solidification point = 52° – 53° C.

EXAMPLE 9

Following the procedure in Example 1, 29.8 g. (0.2 mol) of triethanolamine are added to 48 g (0.5 mol) of furfuraldehyde and 13.5 g of Catalyst 1 (0.05 mol) in a mixture of 300 ml of dimethylformamide and 300 ml of ethanol and the whole is then brought to the reflux temperature while stirring under a stream of nitrogen. After 30 minutes, the dropwise addition of a solution of 26.5 (0.05 mol) of distilled acrylonitrile in a mixture of 50 ml of dimethylformamide and 50 ml of ethanol, over the course of 4½ hours, is started. The mixture is then kept at the same temperature for 20 hours. The solvent mixture is distilled off and the residue is taken up in 300 ml of chloroform. The chloroform solution is then washed with water, dilute sodium bicarbonate solution and twice more with water. It is then dried with magnesium sulphate and after filtering the solution the solvent is distilled off. The residue which remains is distilled in an oil pump vacuum. The α-furoylpropionitrile thus obtained is recrystallized from isopropanol.

Yield: 42.5 g ≙ 57% of theory.
Boiling point$_{0.4}$ = °– 112° C.
Solidification point = 77°– 78° C.

EXAMPLE 10

Following the procedure of Example 1, 13.5 g (0.05 mol) of Cat. 1 are suspended in absolute dimethylformamide and successively 33 g (0.75 mol) of acetaldehyde freshly prepared from paraldehyde and 26.5 g of distilled acrylonitrile (0.5 mol) are added. 20.2 g (0.2 mol) of triethylamine are then added in a slight stream of nitrogen. Thereafter the mixture is stirred for 28 hours at 80° C. For working up, the dimethylformamide is first removed in a waterpump vacuum, and after cooling the residue is filtered. The filtrate is then subjected to fractional distillation. Levulinic acid nitrile of boiling point$_{12}$ = 100 – 103° C is isolated in a yield of 14 g ≙ 29% of theory.

EXAMPLE 11

Following the method described in Example 1, 5.4 g (0.0215 mol) of Cat. 2, 21.2 g (0.2 mol) of distilled benzaldehyde, 14 g (0.2 mol) of distilled methyl vinyl ketone and 300 ml of absolute dimethylformamide are introduced into a 500 ml three-necked flask. After stirring the mixture under nitrogen, 4.3 g (0.04 mol) of sodium carbonate are added. Initially, a dark coloration appears, which disappears in the course of the reaction.

After the addition of the base, the mixture is stirred for 15 hours at 80° C. For working up, the solvent is distilled off under reduced pressure, the residue is dissolved in chloroform and the solution is well washed three times with water. After distilling off the chloroform, the residue is taken up in 50 ml of ethanol, the mixture is left to stand for some time and the benzoin is filtered off. Thereafter the solvent is distilled from the filtrate and the residue is then distilled in vacuo. 1-Phenyl-pentane-(1,4)-dione is isolated.

Yield: 19.1 g ≙ 54% of theory.
Boiling point$_{0.35}$ = 105° C.

EXAMPLE 12

Following the description in Example 1, 5.1 g (approx. 0.02 mol) of Cat. 3, 21.2 g (0.2 mol) of distilled benzaldehyde, 350 ml of dimethylformamide and 14 g (0.2 mol) of stabilized methyl vinyl ketone are introduced into a 500 ml three-necked flask. After displacing the air by pure nitrogen, the mixture is brought to a temperature of 80° C and 14.9 g (0.1 mol) of triethanolamine are added. The mixture is then stirred for 15 hours at the same temperature. Working up takes place as in Example 11 except that the mixture is filtered after having been taken up in chloroform. 1-Phenyl-pentane-1,4-dione is obtained.

Yield: 26 g ≙ 73.5% of theory.
Boiling point$_{0.35}$ = 105° C.

EXAMPLE 13

Following the procedure described in Example 1, 57.2 g (0.275 mol) of benzylideneacetophenone, 29.2 g of benzaldehyde, 25.1 g (0.1 mol) of Catalyst 2 and 400 ml of dimethylformamide are introduced successively into the 500 ml three-necked flask and after stirring for 15 minutes under nitrogen 40.4 g (0.4 mol) of triethylamine are added. The mixture is then heated to 80° C for 12 hours. For working up, the dimethylformamide is distilled off and 150 ml of isopropanol are added to the residue while it is still hot. The product which has precipitated is filtered off, washed with isopropanol and then dried. 2,2,4-Triphenyl-butane-1,4-dione is obtained.

Yield: 72 g ≙ 83.5% of theory.
Melting point: 125 ° – 127° C.

EXAMPLE 14

Following the description in Example 1, 52 g (0.25 mol) of benzylideneacetophenone, 21.2 g (0.20 mol) of benzaldehyde and 11.2 g (0.05 mol) of Catalyst 4 in a mixture of 150 ml of ethanol and 150 ml of dimethylformamide are boiled for 24 hours under reflux after having added 10.1 g (0.1 mol) of triethylamine in the manner indicated. For working up, the mixture is poured into 1½ liters of water and the whole is extracted with 3 × 100 ml of chloroform. The chloroform is then distilled off and 150 ml of isopropanol are added to the residue. The 1,2,4-triphenyl-butane-1,4-dione which has precipitated is isolated and dried.

Yield: 34.8 g ≙ 55.5% of theory.
Solidification point: 125° – 127° C.

EXAMPLE 15

Following the description in Example 1, 52 g (0.25 mol) of benzylideneacetophenone, 21.2 g (0.20 mol) of benzaldehyde and 10.6 g of Catalyst 5 (0.05 mol) are initially introduced into a 500 ml three-necked flask, together with 150 ml of dimethylformamide and 150 ml of ethanol, and after addition of 10.1 g (0.1 mol) of triethylamine, as described above, the mixture is heated at the reflux temperature under nitrogen for 24 hours and worked up as described in Example 14.

Yield: 42 g ≙ 67% of theory of pure 1,2,4-triphenylbutane-1,4-dione.

EXAMPLE 16

Following the procedure described in Example 1, 9.6 g (0.1 mol) of furfuraldehyde and 2.5 g (0.01 mol) of Catalyst 2 in 100 ml of absolute dimethylformamide are initially introduced into a 250 ml three-necked flask and the mixture is brought to 80° C internal temperature. Thereafter a solution of 16.7 g (0.1 mol) of 2-(α-furoyl)-ethyldimethylamine is added dropwise over the course of 4½ hours in a slight stream of nitrogen. The mixture is then stirred for a further 8 hours in a slight stream of nitrogen. For working up, the mixture is cooled and stirred into 1 liter of water, and the whole is acidified with a little dilute sulphuric acid. The crude product which has precipitated is filtered off and recrystallized from ethanol with addition of about 1 g of active charcoal. The resulting product, 1,4-di-(2'-furyl)-butane-1,4-dione, forms glass-clear crystals of high refractive index.

Yield: 11.1 g ≙ 51% of theory.
Melting point: 131° – 133° C.

EXAMPLE 17

Following the procedure described in Example 1, 39.6 g (0.2 mol) of 1-(2'-furyl)-3-phenyl-prop-2-en-1-one, 19.2 g (0.2 mol) of furfuraldehyde and 5.0 g (0.02 mol) of catalyst 2 are dissolved successively in 350 ml of absolute dimethylformamide in a 500 ml three-necked flask and after adding 4 g (0.04 mol) of triethylamine the mixture is kept for 15 hours at 75° C while stirring under nitrogen. For working up, the mixture is cooled and stirred into 1½ liters of water containing about 10 g of sodium bicarbonate. It is then extracted with 5 × 100 ml portions of chloroform. The organic layers are combined, the solvent is distilled off and 100 ml of isopropanol are added to the liquid residue. This mixture is left to stand for 12 hours and the product is then filtered off and dried. 2-Phenyl-1,4-(2'-butane-1,4-dione is obtained.

Yield: 43 g ≙ 73% of theory
Melting point: 109° – 110° C.
$C_{18}H_{14}O_4$ (molecular weight 294.3).
Calculated: C, 73.46, H, 4.80.
Found: C, 73.39, H, 4.73.

EXAMPLE 18

Following the description in Example 1 and 6, 325 ml of dimethylformamide, 75 ml of distilled water, 6.8 g (0.025 mol) of Catalyst 1, 18.7 g (0.26 mol) of n-butyraldehyde and 52 g (0.25 mol) of benzylideneacetophenone are successively introduced into a three-necked flask. The mixture is then stirred at 80° C under nitrogen and 10.1 g (0.1 mol) of triethylamine are added. The whole is stirred for 15 hours at 80° C and worked up as described in Example 6. On fractionation, a fraction of boiling point$_{0.25}$ = 160° – 165° C is obtained.

Yield: 43.5 g ≙ 62% of theory of pure 1,3-diphenyl-1,4-dioxoheptane.

EXAMPLE 19

Analogously to the procedure described in Example 1, 19.2 g (0.2 mol) of furfuraldehyde, 5 g (0.02 mol) of Catalyst 2 and 41.5 g (0.2 mol) of benzylideneacetophenone are initially introduced into 350 ml of dimethylformamide and after stirring for 10 minutes while passing in nitrogen, 5 g (0.05 mol) of triethylamine are added. After 12 hours at 70° C, the solvent is removed in a waterpump vacuum and 150 ml of iso-propanol are added to the residue while it is still hot. After crystallization has taken place, the product is filtered off, washed with a little i-propanol and then dried. 1-(2'-Furyl)-2,4-diphenyl-1,4-dioxobutane is obtained.

Yield: 48 g ≙ 79% of theory.
Melting point: 115° – 116° C.

EXAMPLE 20

A mixture of 36 g (1.0 mol) of distilled n-butyraldehyde, 13.5 g (0.05 mol) of Catalyst 1, 400 ml of dimethylformamide and 20.2 g (0.2 mol) of triethylamine is initially introduced, under nitrogen, into the apparatus described in Example 1. The mixture is stirred for 2 hours at 80° C and a solution of 26.5 g (0.5 mol) of distilled acrylonitrile is then added dropwise over the course of 6 hours. The whole is then stirred for a further 16 hours at the same temperature. For working up, the solvent is distilled off in vacuo, the oil which remains is taken up in chloroform and the solution is washed with water, dilute sodium bisulphite solution and again with water. The organic layer is separated off and dried with magnesium sulphate. It is filtered, solvent is distilled off and the residue is distilled in a water-pump vacuum. 4-Oxo-heptane-1-carbonitrile is obtained.

Yield: 24 g ≙ 54% of theory.
Boiling point$_{12}$ = 124° – 127° C.

EXAMPLE 21

Following the procedure described in Example 1, 13.5 g (0.05 mol) of Cat. 1, 43.1 g (0.5 mol) of n-valeraldehyde, 35.1 g (0.5 mol) of methyl vinyl ketone, 500 ml of ethanol and 20.2 g (0.2 mol) of triethylamine are heated for 12 hours under nitrogen at the reflux temperature. For working up, the solvent is distilled, the cooled residue is taken up in chloroform, the chloroform phase is washed with dilute sulphuric acid and subsequently with water, the chloroform is removed and the liquid residue is distilled in a waterpump vacuum. Nonane-2,5-dione is obtained.

Boiling point$_{12}$ = 106° – 108° C.
Yield: 53.5 g = 68% of theory.

EXAMPLE 22

Following the procedure described in Example 21, 2.7 g (0.01 mol) of Cat. 1, 43.1 g (0.5 mol) of n-valeraldehyde, 35.1 g (0.5 mol) of methyl vinyl ketone, 500 ml of ethanol and 4.4 g (0.0436 mol) of triethylamine are employed in the reaction in the present case.

After appropriate working up as in Example 21, distillation gives nonane-2,5-dione.

Boiling point$_{12}$ = 106° – 108° C.
Yield: 40.8 g = 52% of theory.

EXAMPLE 23

34.9 g (0.6 mol) of propionaldehyde, 35.1 g (0.5 mol) of methyl vinyl ketone, 13.5 g (0.05 mol) of Cat. 1, 500 ml of ethanol and 20.2 g (0.2 mol) of triethylamine are reacted analogously to the procedure described in Example 1. In the present case, a high-efficiency condenser is required.

The mixture is heated for 15 hours under pure nitrogen at the reflux temperature, while stirring, For working up, the solvent is removed, 100 ml of THF are added to the cooled residue to give a suspension, the solid is filtered off and the triethylamine hydrochloride is freed from remnants of product. The THF is removed from the filtrate and the residue is fractionated in a waterpump vacuum. Heptane-2,5-dione is obtained.

Boiling point$_{12}$ = 76° – 78° C.
Yield: 38.6 g = 60% of theory.

EXAMPLE 24

64.1 g (0.5 mol) of caprylaldehyde, 35.1 g (0.5 mol) of methyl vinyl ketone, 13.5 g (0.05 mol) of Cat. 1 and 20.2 g (0.2 mol) of triethylamine in 500 ml of ethanol are reacted as described in Example 1.

The product is worked up as described in Example 21. On fractionation, dodecane-2,5-dione of boiling point$_{0.4 - 0.3}$ = 100° C is obtained.

Yield: 69.4 g = 70% of theory.
Melting point; 40° – 41° C (recrystallization from methanol; allow crystallization to take place at 0° C).

EXAMPLE 25

78.1 g (0.5 mol) of caprinaldehyde, 35.1 g (0.5 mol) of methyl vinyl ketone, 13.5 g (0.05 mol) of Cat. 1, 500 ml of ethanol and 40.4 g of triethylamine (0.4 mol) are allowed to react in the manner described in Example 1. The product is worked up as described in Example 21 (recrystallization from CH$_3$OH).

Product: tetradecane-2,5-dione.
Boiling point$_{0.35}$ = 117° C.
Yield: 77.2 g = 68% of theory.
Melting point = 52° – 53° C.

EXAMPLE 26

78.1 g (0.5 mol) of caprinaldehyde, 35.1 g (0.5 mol) of methyl vinyl ketone and 13.5 g (0.05 mol) of Cat. 1 are introduced into a 250 ml three-necked flask equipped with a stirrer, reflux condenser (high efficiency, KOH drying tube) and N$_2$ inlet. After adding 40.4 g (0.4 mol) of triethylamine, a N$_2$ atmosphere is set up, the mixture is stirred and the surrounding oil bath is brought to 80° C. The initially undissolved catalyst dissolves and after some time triethylamine hydrochloride precipitates. The mixture is kept at 80° C for 12 hours. For working up, it is first cooled, and then the procedure described in Example 21 is followed. Tetradecane-2,5-dione is obtained. Recrystallization from methanol.

Yield: 87.6 g = 77.5% of theory.
Boiling point$_{0.35}$ = 117° C.
Melting point = 52° – 53° C.

EXAMPLE 27

184.3 g of laurinaldehyde (50% strength by weight solution in phthalic acid dimethyl ester) (= 0.5 mol of laurinaldehyde), 35.1 g (0.5 mol) of methyl vinyl ketone, 13.5 g (0.05 mol) of Cat. 1, 1,000 ml of ethanol and 20.2 g (0.2 mol) of triethylamine are brought together in the manner described in Example 1. After 15 hours' reaction time, the product is worked up as described in Example 21.

Initially, a first running of boiling range: b.p.$_{0.3 - 0.2}$ = 90° – 128° C is separated off, and thereafter hexadecane-2,5-dione distils at boiling point$_{0.2}$ = 128° – 129° C.

Yield: 96.1 g = 76% of theory.
Melting point = 62° – 63° C.

C$_{16}$H$_{30}$O$_2$ molecular weight: 254.40.
Calculated: C, 75.53, H, 11.89.
Found: C, 75.88, H, 12.02.

EXAMPLE 28

67.1 g (0.5 mol) of hydrocinnamaldehyde, 35.1 g (0.5 mol) of methyl vinyl ketone, 13.5 g (0.05 mol) of Cat. 1, 20.2 g (0.2 mol) of triethylamine and 500 ml of ethanol are brought together, in the manner described in Example 1. The product is worked up as described in Example 21. Fractional distillation gives 1-phenyl-heptane-3,6-dione.

Boiling point$_{0.3 - 0.4}$ = 122°–124° C.
Yield: 61.8 g = 60% of theory.
C$_{13}$H$_{14}$O$_2$ molecular weight 202.24.
Calculated: C, 77.20; H, 6.98.
Found: C, 77.40; H, 7.14.

EXAMPLE 29

The reaction is carried out analogously to Example 28, with 2-phenylpropanal instead of 3-phenylpropanal.

2-Phenyl-heptane-3,6-dione is obtained by fractional distillation.

Boiling point$_{0.3}$ = 109°–111° C.
Yield: 61.2 g = 59% of theory.

EXAMPLE 30

53 g (0.5 mol) of benzaldehyde, 35.1 g (0.5 mol) of methyl vinyl ketone, 12.6 g (0.05 mol) of Cat. 2 and 30.3 g of triethylamine are mixed in the manner described in Example 26. After about 10 minutes, triethylamine hydrochloride precipitates. After a total of 5 hours, the product is worked up as described in Example 21.

1-Phenyl-pentane-1,4-dione is obtained.
Boiling point $_{0.4}$ = 109° C.
Yield: 57.5 g = 65.3% of theory.
Melting point = 31° C.

The yield can be increased by about 10% by lengthening the reaction time by 7 hours and carrying out the reaction at 60° C.

EXAMPLE 31

70.3 g (0.5 mol) of o-chlorobenzaldehyde, 35.1 g (0.5 mol) of methyl vinyl ketone, 12.6 g (0.05 mol) of Cat. 2 and 30.3 g (0.3 mol) of triethylamine are brought together in the manner described in Example 26. After 2 hours' reaction time, the mixture is worked up as described in Example 21.

1-(o-chlorophenyl)-pentane-1,4-dione is obtained.
Yield: 54.4 g = 52% of theory.

A yield which is about 10% higher can be obtained by working at 60° C and extending the reaction time by 10 hours.

EXAMPLE 32

200 ml of ethanol are slowly added dropwise, while stirring, to 1.1 g (0.05 mol) of sodium in a 1 l three-necked flask equipped with a stirrer, reflux condenser (with NaOH drying tube) and dropping funnel. After the sodium has completely dissolved, the mixture is cooled to room temperature and 16.9 g (0.05 mol) of Cat. 6 are added and rinsed down with a little ethanol. After the solution has turned white due to the sodium chloride which has separated out, 48 g (0.5 mol) of furfuraldehyde, 35.1 g (0.5 mol) of methyl vinyl ketone, 500 ml of ethanol and 20.2 g (0.2 mol) of triethylamine are added successively. The further treatment is carried out as in Example 1. After 15 hours' reaction time, the mixture is worked up as described in Example 21.

1-(2'-Furyl)-pentane-1,4-dione was obtained.
Yield: 61.7 g =76% of theory.
Boiling point$_{0.4}$ = 98°–100° C.
Melting point = 48°–49° C.

EXAMPLE 33

35.1 g (0.125 mol) of dibenzylideneacetone, 24 g (0.25 mol) of furfuraldehyde, 6.8 g (0.025 mol) of Cat. 1, 250 ml of ethanol and 10.1 g (0.1 mol) of triethylamine are brought together as desired in Example 1. The mixture is heated under reflux for 12 hours. After about 1 hour, the product begins to precipitate. The initially dark red color disappears slowly. For working up, the produce is cooled to 0° C, filtered off and washed with ethanol until pure. It is dried, finally in a drying pistol.

Yield: 31.8 g = 54% of theory of 1,7-di-(2'-furyl)-2,6-diphenyl-heptane-1,4,7-trione.
Melting point = 226°– 228° C.
$C_{27}H_{22}O_5$, molecular weight: 248. Calculated: C, 76.04; H, 5.20. Found: C, 75.80; H, 5.27.

EXAMPLE 34

66.1 g (0.5 mol) of trans-cinnamaldehyde, 35.1 g (0.5 mol) of methyl vinyl ketone and 500 ml of ethanol are introduced into a 1 l three-necked flask equipped with a stirrer, reflux condenser (with KOH drying tube) and dropping funnel with pressure equilibrator (for the $N_2$ inlet). The dropping funnel contains a solution of 13.5 g (0.05 mol) of Cat. 1 in 200 ml of ethanol, to which 20.2 g (0.2 mol) of triethylamine were added shortly before use. The mixture is now heated to the reflux temperature in a $N_2$ atmosphere. The dropwise addition is now started (about 0.5 drop per second, so that the addition lasts 7 to 8 hours). The product is worked up in the manner described in Example 21. After separating off some first runnings, a fraction of boiling point$_{0.4}$ = 145°–148° C is obtained.

Yield: 40.5 g = 40% of theory of trans-1-phenyl-hept-1-ene-3,6-dione.
Melting point = 46°– 48° C. The product is recrystalized from ether/pentane.
$C_{13}H_{14}O_2$ Molecular weight: 202.24. Calculated: C, 77.20; H, 6.98. Found: C, 77.03; H, 6.77.

EXAMPLE 35

20.8 g (0.1 mol) of β,β-diphenylacrolein, 7.0 g (0.1 mol) of methyl vinyl ketone, 2.7 g (0.01 mol) of Cat. 1, 100 ml of ethanol and 4 g (0.04 mol) of triethylamine are combined, and heated for 12 hours under reflux, in the manner described in Example 1. The product is worked up as described in Example 21.
Boiling point$_{0.15}$ = 174°–176° C.
Yield: 20.0 g = 72% of theory.

The 1,1-diphenyl-hept-1-ene-3,6-dione obtained can be recrystallized easily from isopropanol.
Melting point = 85°– 87° C.
$C_{19}H_{18}O_2$ Molecular weight = 278.33. Calculated: C, 81.98; H, 6.52. Found: C, 82.15; H, 6.42.

EXAMPLE 36

76.1 g (0.6 mol) of citral (a mixture of the cis and trans isomers of 3,7-dimethyl-octa-2,6-dien-1-al), 35.1 g (0.5 mol) of methyl viny ketone, 13.5 g (0.05 mol) of Cat. 1, 500 mol of ethanol and 20.2 g (0.2 mol) of triethylamine are brought together in the manner described in Example 1. After 13 hours' reaction time, the solvent is distilled off, the oil which remains is taken up in $CHCl_3$ and the solution is washed with dilute $NaHCO_3$ solution. It is then washed with water, the chloroform is distilled off and the residue is fractionated. After separating off some first runnings, a fraction consisting of 7,11-dimethyl-dodeca-6,10-diene-2,5-dione is obtained.

Boiling point$_{0.3}$ = 108°–111° C.
Yield: 58.8 g = 53% theory.

EXAMPLE 37

33.5 g (0.25 mol) of terephthalaldehyde, 35.1 g (0.50 mol) of methyl vinyl ketone, 12.6 g (0.05 mol) of Cat. 2, 500 ml of ethanol and 30.3 g (0.3 mol) of triethylamine are brought together in the manner described in Example 1. The reaction time is 15 hours at the reflux temperature. For working up, the product is cooled with an ice-sodium chloride mixture, filtered off and washed with ethanol. The product is dried in a drying pistol at 60° C.

Yield: 19.8 g = 29% of theory of 1,1'-p-phenylene-di-(pentane-1,4-dione).
Melting point = 150°–152° C.
$C_{16}H_{18}O_4$ Molecular weight: 274.3. Calculated: C, 70.05; H, 6.61. Found: C, 69.89; H, 6.78.

EXAMPLE 38

32,1 (0.15 mol) of di-(2'-furylidene)-acetone, 28.8 g (0.3 mol) of furfuraldehyde, 4.1 g (0.015 mol) of Cat. 1, 300 ml of ethanol and 6.6 g (0.06 mol) of triethylamine are brought together in the manner described in Example 1. The reaction time is 5 hours. Thereafter the mixture is cooled and the solid which has precipitated is filtered off. The resulting product is washed with ethanol and then dried.

Yield: 27 g = 44.3% of theory of 1,2,6,7-tetra-(2'-furyl)-heptane-1,4,7-trione.
Melting point = 146°– 148° C.
$C_{23}H_{16}O_7$ Molecular weight: 406.37. Calculated: C, 67.97, H, 4.46. Found: C, 67.87; H, 4.38.

EXAMPLE 39

25 g (0.25 mol) of glutarodialdehyde, 35.1 g (0.5 mol) of methyl vinyl ketone, 13.5 g (0.05 mol) of Cat. 1 and 30.3 g (0.3 mol) of triethylamine are combined in the manner described in Example 26. The surrounding oil bath is set to a temperature of 70° C. The reaction time is 13 hours. The mixture is worked up as described in Example 21. Tridecane-2,5,9,12-tetrone has a boiling range of boiling point $_{0.6}$ = 180°–185° C. The product is crystallized from isopropanol.

Yield: 13.8 g = 23% of theory.
Melting point = 103°– ψ° C
$C_{13}H_{20}O_4$ Molecular weight: 240.63. Calculated: C, 64.98; H, 8.39. Found: C, 64.90; H, 8.40.

EXAMPLE 40

48 g (0.5 mol) of furfuraldehyde, 13.5 g (0.05 mol) of Cat. 1, 90.5 g (0.5 mol) of β-bromopropionic acid ethyl ester and 100 ml of dried THF are combined in the manner described in Example 1. 80.8 g (0.8 mol) of triethylamine are added dropwise, as rapidly as possible, at the boiling point of the solvent. After the initially vigorous reaction has ended, the mixture is additionally heated for 10 hours. The THF is then distilled off and the residue worked up in the manner described in Example 21. Distillation gives a fraction of boiling point$_{0.5}$ = 115°– 118° C which is β-furoylpropionic acid ethyl ester.

Yield: 37 g = 38% of theory
Melting point = 52°– 53° C

EXAMPLE 41

57.1 g (0.5 mol) of oenanthaldehyde, 35.1 g (0.5 mol) of pure methyl vinyl ketone, 13.5 g of Cat. 1 and 30.3 g (0.3 mol) of absolute distilled triethylamine are brought together in the manner described in Example 26. After a reaction time of 12 hours in a nitrogen atmosphere at a temperature of the oil bath of 80° C, the mixture is worked up in the manner described in Example 21. On subsequent fractionation, undecane-1,5-dione is obtained.

Yield: 71.7 g = 78% of theory
Boiling point$_8$ = 128° C
Melting point = 33°-34° C

EXAMPLE 42

22.4 g (0.2 mol) of cis-hept-4-en-1-al, 14 g (0.2 mol) of methyl vinyl ketone, 5.4 g (0.02 mol) of Cat. 1 and 12.0 g (0.12 mol) of triethylamine are brought together in the manner described in Example 26. After 12 hours' reaction time at a temperature of the oil bath of 80° C the mixture is worked up in the manner described in Example 21. On subsequent fractionation, cis-undec-8-ene-2,5-dione is obatined.

Boiling point$_{0.4}$ = 81° C
Yield: 27.6 g = 76% of theory
$C_{11}H_{18}O_2$ (182.3). Calculated: C, 72.49, H, 9.96. Found: C, 72.50, H, 10.01.

EXAMPLE 43

22.0 g (0.2 mol) of hept-4-in-1-al, 14 g (0.2 mol) of methyl vinyl ketone, 5.4 g (0.02 mol) of Cat. 1 and 12.6 g (0.12 mol) of triethylamine are brought together in the manner described in Example 26. After 12 hours' reaction time at a surrounding temperature of 80° C in a nitrogen atmosphere, the mixture is worked up in the manner described in Example 21. On subsequent fractionation, undec-8-ine-2,5-dione is obtained.

Boiling point$_{0.5}$ = 85° C
Yield: 28.0 g = 78% of theory

EXAMPLE 44

73.1 g (0.5 mol) of benylideneacetone, 43 g (0.5 mol) of valeraldehyde, 12.6 g (0.05 mol) of Cat. 2, 30.3 g (0.3 mol) of triethylamine and 100 ml of ethanol are brought together, and heated for 12 hours under reflux, in the manner described in Example 1.

The mixture is worked up analogously to Example 21. Fractionation gives 42.3 g of 4-phenyl-nonane-2,5-dione.

Boiling point$_{0.35}$ = 108°–110° C
Yield: 42.3 g = 37.5% of theory.

EXAMPLE 45

48 g (0.5 mol) of furfuraldehyde, 73.1 g of benzylideneacetone (0.5 mol), 12.6 g (0.05 mol) of Cat. 2, 30.3 g of triethylamine and 100 ml of ethanol are combined, and heated for 12 hours under reflux, in the manner described in Example 1. The mixture is worked up as in Example 21. Fractionation gives 1-(2'-furyl)-2-phenyl-pentane-1,4-dione.

Boiling point$_{0.3 - 0.2}$ = 145°–142° C

Yield: 97.0 g = 80% of theory
Melting point = 66°–67° C.

We claim:
1. Process for the preparation of a ketone comprising reacting an unsaturated compound of the formula

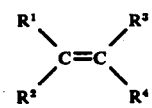

wherein
R$^1$, R$^2$ and R$^3$ are identical or different and represent hydrogen or an optionally substituted C$_{1-12}$ aliphatic, C$_{3-18}$ cycloaliphatic, C$_{6-18}$ araliphatic with C$_{1-6}$ in the aliphatic moiety, phenyl, naphthyl or heterocyclic radical or a carboxylic acid ester group,
R$^4$ represents the nitrile radical, or the group —CO—R$^5$ or —CO—O—R$^5$
wherein
R$^5$ denotes an optionally substituted aliphatic, araliphatic, aromatic or heterocyclic radical
or wherein
it is also possible for any of R$^1$ and R$^2$ or R$^3$, R$^2$ and R$^4$, and R$^3$ and R$^4$ to be bonded to one another directly, with formation of a carbocyclic or heterocyclic ring,
with an aldehyde in the presence of a weak base other than cyanide and, as catalyst, a quaternary ammonium salt of the formula

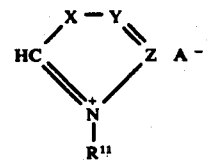

wherein
X represents oxygen, sulphur, selenium or the —NR$^{12}$— group,
Y and Z are identical or different and each represents an optionally substituted carbon atom or nitrogen atom,
R$^{11}$ and R$^{12}$ are identical or different and each represents a C$_1$ and C$_{12}$ aliphatic radical, a C$_5$ to C$_{12}$ cycloaliphatic radical, a C$_6$ to C$_{12}$ araliphatic radical which contains up to 6 carbon atoms in the aliphatic part, a C$_6$ to C$_{10}$ aromatic radical or a 5-membered ring which in addition to the carbon atoms contains an oxygen and/or a sulphur atom, and
A represents an acid radical other than cyanide.

2. Process according to claim 1 wherein the unsaturated compound is prepared in situ from a Mannich base of the formula

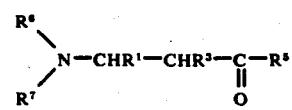

wherein
R$^6$ and R$^7$ are identical or different and represent an aliphatic radical or can also be linked directly to one another.

3. Process according to claim 1 wherein the unsaturated compound is prepared in situ from a β-halogenocarbonyl compound of the formula

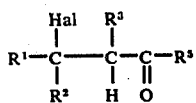

wherein
Hal represents chlorine, bromine or iodine.

4. Process according to claim 1, wherein the aldehyde is a compound of the formula

wherein
R⁸ represents hydrogen or an optionally substituted $C_{1-20}$ aliphatic, $C_{3-18}$ cycloaliphatic, $C_{7-18}$ araliphatic with $C_{1-6}$ in the aliphatic moiety, phenyl, naphthyl or heterocyclic radical.

5. Process according to claim 4 wherein the aldehyde is prepared in situ from the corresponding acyloin or benzoin of the formula

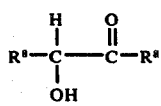

6. Process according to claim 4 wherein R⁸ represents a $C_1$ to $C_{12}$ aliphatic radical, a $C_5$ to $C_{12}$ cycloaliphatic radical, a $C_6$ to $C_{12}$ araliphatic radical which contains up to 6 carbon atoms in the aliphatic part, a $C_6$ to $C_{10}$ aromatic radical to a 5-membered ring which in addition to the carbon atoms contains an oxygen and/or a sulphur atom.

7. Process according to claim 4 wherein R⁸ represents a methyl, ethyl, cyclohexyl, benzyl, 1-methylenenaphthyl, phenyl, naphthyl or furfuryl radical.

8. Process according to claim 1 wherein the quaternary ammonium salt is a thiazolium salt, imidazolium salt, benzimidazolium salt, selenazolium salt, triazolium salt, oxidazolium salt or thiadiazolium salt.

9. Process according to claim 1 wherein the base is a basic salt of an alkali metal or of an alkaline earth metal.

10. Process according to claim 1, wherein the base is an amine of the formula

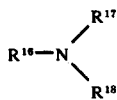

wherein
R¹⁶, R¹⁷ and R¹⁸ are identical or different and each is a $C_1$ to $C_{12}$ aliphatic radical, a $C_5$ to $C_{12}$ cycloaliphatic radical, a $C_6$ to $C_{12}$ araliphatic radical which contains up to 6 carbon atoms in the aliphatic part, a $C_6$ to $C_{10}$ aromatic radical or a 5-membered ring which in addition to the carbon atoms contains an oxygen and/or a sulphur atom.

11. Process according to claim 1 wherein the reaction is carried out in a polar solvent.

12. Process according to claim 1 wherein the unsaturated compound and the aldehyde are reacted in about equimolar quantities.

13. Process according to claim 1 wherein the reaction is carried out in the presence of from 1 to 50 mol % of the quaternary ammonium compound, relative to the aldehyde.

14. Process according to claim 1 wherein the reaction is carried out in the presence of from 3 to 5 mols of base per mole of the quaternary ammonium compound.

15. Process according to claim 1 wherein the reaction is effected at a temperature of from −10° to 100° C.

16. Process according to claim 1 wherein R¹, R², R³ and R⁵ individually represent straight or branched chain aliphatic radicals having up to 12 carbon atomms, cycloaliphatic radicals having from 3 to 18 carbon atoms, aliphatic benzene having from 1 to 6 carbon atoms in the aliphatic part, aromatic radicals of the benzene series, heterocyclic radicals having 5- or 6-membered rings containing one or more nitrogen, oxygen or sulphur atoms, or two of the radicals R¹, R², R³ and R⁴ are linked to form a saturated or unsaturated heterocyclic or carbocyclic 5-or 6-membered ring.

17. Process according to claim 1 wherein one or more of the radicals R¹, R², R³ and R⁵ are substituted by a halogen atom or a hydroxy, cyano, nitro, amino, alkyl amino, arylamino, alkyl, aryl, alkoxy alkylmercapto, carboxylic acid ester, thiocarboxylic acid ester, alkylcarbonyl or arylcarbonyl radical.

18. Process according to claim 4 wherein the quaternary ammonium salt is a compound of the formula

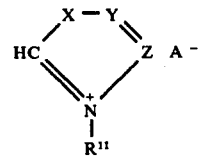

and the base is a basic salt of an alkali metal or of an alkaline earth metal or an amine of the formula
wherein
X represents oxygen, sulphur, selenium or the —NR¹²— group,
Y and Z are identical or different and each represents an optionally substituted carbon atom or nitrogen atom,
R¹¹, R¹², R¹⁶, R¹⁷ and R¹⁸ are identical or different and each represents a $C_1$ to $C_{12}$ aliphatic radical, a $C_5$ to $C_{12}$ cycloaliphatic radical, a $C_6$ to $C_{12}$ araliphatic radical which contains up to 6 carbon atoms in the aliphatic part, a $C_6$ to $C_{10}$ aromatic radical or a 5-membered ring which in addition to the carbon atoms contains an oxygen, and/or a sulphur atom, the reaction being effected in a polar solvent at from −10° to 100° C with about an equimolar amount of unsaturated compound and aldehyde, about 1 to 50 mol % of quaternary ammonium compound based on aldehyde and 3 to 5 mols of base per mol of quaternary ammonium compound.

* * * * *

UNITED STATES PATENT AND TRADEMARK OFFICE
CERTIFICATE OF CORRECTION

PATENT NO. : 4,035,395  
DATED : July 12, 1977  
INVENTOR(S) : Hermann Stetter, et al.

Page 1 of 2

It is certified that error appears in the above-identified patent and that said Letters Patent are hereby corrected as shown below:

| | |
|---|---|
| Col. 2, line 55 | cancel "groups" and substitute --group-- |
| Col. 3, line 66 | insert -- V -- |
| Col. 5, line 25 | insert " ´ " over "A" in "pelargonald..." |
| Col. 5, line 56 | cancel "captronin" and substitute --capronoin-- |
| Col. 10, line 64 | after "by" insert --nitrogen-- |
| Col. 11, line 38 | before "°-112°C" insert --108-- |
| Col. 13, line 42 | after "(2'- " insert --furyl)-- |
| Col. 17, line 14 | cancel "desired" and substitute --described-- |
| Col. 17, line 68 | cancel "viny" and substitute --vinyl-- |

UNITED STATES PATENT AND TRADEMARK OFFICE
CERTIFICATE OF CORRECTION

PATENT NO. : 4,035,395
DATED : July 12, 1977
INVENTOR(S) : Hermann Stetter, et al.

It is certified that error appears in the above-identified patent and that said Letters Patent are hereby corrected as shown below:

Col. 18, line 1         cancel "mol" and substitute --ml--

Col. 18, line 56        cancel "$\mu°C$" and substitute -- -104°C --

Col. 20, line 19        before "$R^4$" insert --and--

Col. 20, line 48        cancel "$C_1$ and $C_{12}$" and substitute --$C_1$ to $C_{12}$--

Col. 22, line 20        cancel "atomms" and substitute --atoms--

Col. 22, line 31        after "alkoxy" insert -- , --

Signed and Sealed this

Fourteenth Day of February 1978

[SEAL]

Attest:

RUTH C. MASON
Attesting Officer

LUTRELLE F. PARKER
Acting Commissioner of Patents and Trademarks